United States Patent
Hayam et al.

(10) Patent No.: US 10,105,073 B2
(45) Date of Patent: Oct. 23, 2018

(54) FLEXIBLE MULTIPLE-ARM DIAGNOSTIC CATHETER

(71) Applicant: BIOSENSE WEBSTER (ISRAEL) LTD., Yokneam (IL)

(72) Inventors: Gal Hayam, Tivon (IL); Stuart G. Williams, Ontario (CA)

(73) Assignee: BIOSENSE WEBSTER (ISRAEL) LTD, Yokneam (IL)

(*) Notice: Subject to any disclaimer, the term of this patent is extended or adjusted under 35 U.S.C. 154(b) by 767 days.

(21) Appl. No.: 14/086,294

(22) Filed: Nov. 21, 2013

(65) Prior Publication Data
US 2015/0141785 A1    May 21, 2015

(51) Int. Cl.
| | |
|---|---|
| A61B 5/04 | (2006.01) |
| A61B 18/18 | (2006.01) |
| A61B 5/042 | (2006.01) |
| A61B 18/14 | (2006.01) |
| A61B 5/00 | (2006.01) |
| A61B 18/00 | (2006.01) |

(52) U.S. Cl.
CPC .......... *A61B 5/0422* (2013.01); *A61B 5/4836* (2013.01); *A61B 5/6857* (2013.01); *A61B 5/6859* (2013.01); *A61B 18/1492* (2013.01); *A61B 2018/0016* (2013.01); *A61B 2018/00357* (2013.01); *A61B 2018/00577* (2013.01); *A61B 2018/00839* (2013.01); *A61B 2018/1435* (2013.01)

(58) Field of Classification Search
CPC ...... A61B 18/1492; A61B 2018/00577; A61B 2018/00404; A61B 2018/00267; A61B 2018/1435; A61B 2018/1475; A61B 5/6852; A61M 2205/0266

USPC ................ 600/372–374, 377, 381, 393, 435, 600/508–509; 606/20–42
See application file for complete search history.

(56) References Cited

U.S. PATENT DOCUMENTS

| | | | |
|---|---|---|---|
| 5,282,845 A | * | 2/1994 | Bush .................... A61N 1/0587 607/127 |
| 5,391,199 A | | 2/1995 | Ben Haim |
| 5,855,592 A | * | 1/1999 | McGee ................ A61N 1/3622 600/374 |
| 6,239,724 B1 | | 5/2001 | Doron |
| 6,332,089 B1 | | 12/2001 | Acker |
| 6,484,118 B1 | | 11/2002 | Govari |

(Continued)

FOREIGN PATENT DOCUMENTS

| | | |
|---|---|---|
| CN | 102949176 A | 3/2013 |
| WO | WO 96/05768 A1 | 2/1996 |

OTHER PUBLICATIONS

Ouyang et al. Complete Isolation of Left Atrium Surrounding the Pulmonary Veins: New Insights From the Double-Lasso Technique in Paroxysmal Atrial Fibrillation. Circulation Oct. 12, 2004;110(15):2090-6. Epub Oct. 4, 2004.

(Continued)

*Primary Examiner* — Joseph Stoklosa
*Assistant Examiner* — Brian M Antiskay
(74) *Attorney, Agent, or Firm* — Louis J. Capezzuto

(57) ABSTRACT

A medical probe includes a distal end and an elongate body for insertion into an organ of a patient. The distal end is connected to the elongate body and includes multiple arms that, when inserted into the organ, extend to form multiple respective spirals each having electrodes disposed thereon.

26 Claims, 2 Drawing Sheets

(56) References Cited

U.S. PATENT DOCUMENTS

| | | | |
|---|---|---|---|
| 6,618,612 B1 | 9/2003 | Acker | |
| 6,684,109 B1* | 1/2004 | Osypka | A61N 1/0563 607/122 |
| 6,690,963 B2 | 2/2004 | Ben Haim | |
| 6,771,996 B2* | 8/2004 | Bowe | A61B 18/1492 600/374 |
| 6,805,704 B1 | 10/2004 | Hoyns | |
| 7,561,907 B2* | 7/2009 | Fuimaono | A61B 5/0422 600/374 |
| 7,740,629 B2* | 6/2010 | Anderson | A61B 18/1492 600/374 |
| 8,620,399 B2* | 12/2013 | Gonda | A61B 5/042 29/825 |
| 8,712,550 B2* | 4/2014 | Grunewald | A61B 18/1492 600/381 |
| 9,084,869 B2* | 7/2015 | Anderson | A61M 25/0041 |
| 9,351,789 B2* | 5/2016 | Novichenok | A61B 18/1492 |
| 9,579,149 B2* | 2/2017 | Kelly | A61B 18/1492 |
| 9,717,557 B2* | 8/2017 | Salahieh | A61B 1/313 |
| 9,750,422 B2* | 9/2017 | Zino | A61B 5/0422 |
| 2001/0007070 A1 | 7/2001 | Stewart et al. | |
| 2002/0052604 A1 | 5/2002 | Simon | |
| 2002/0065455 A1 | 5/2002 | Ben Haim | |
| 2002/0111618 A1* | 8/2002 | Stewart | A61B 18/1492 606/41 |
| 2002/0165441 A1 | 11/2002 | Coleman et al. | |
| 2003/0120150 A1 | 6/2003 | Govari | |
| 2004/0068178 A1 | 4/2004 | Govari | |
| 2005/0101852 A1* | 5/2005 | Bautista | A61B 5/0422 600/372 |
| 2008/0255539 A1* | 10/2008 | Booth | A61B 18/1492 604/526 |
| 2010/0036285 A1 | 2/2010 | Govari et al. | |
| 2010/0198041 A1 | 8/2010 | Christian et al. | |
| 2012/0245577 A1* | 9/2012 | Mihalik | A61B 18/1492 606/33 |
| 2012/0245665 A1 | 9/2012 | Friedman | |
| 2012/0290053 A1 | 11/2012 | Zhang et al. | |
| 2013/0253504 A1* | 9/2013 | Fang | A61B 18/1492 606/41 |
| 2013/0274582 A1 | 10/2013 | Afonso et al. | |
| 2014/0257069 A1* | 9/2014 | Eliason | A61B 5/6858 600/373 |

OTHER PUBLICATIONS

European Search Report dated Mar. 26, 2015 for corresponding Application No. EP14194008.
EP14194008.0 Exam Report dated May 3, 2016.

* cited by examiner

FLEXIBLE MULTIPLE-ARM DIAGNOSTIC CATHETER

FIELD OF THE INVENTION

The present invention relates generally to medical devices, and particularly to methods and systems for diagnostic medical probes.

BACKGROUND OF THE INVENTION

Invasive medical probes are used in a variety of medical procedures, such as cardiac electrophysiological (EP) mapping and ablation. For example, U.S. Pat. No. 7,740,629, whose disclosure is incorporated herein by reference, describes an ablation catheter including an elongate carrier. A first loop is arranged at, or adjacent, a distal end of the carrier. At least one sensing electrode is carried on the first loop for sensing irregular electrical activity in a patient's body. At least one further loop is arranged proximally relative to the first loop on the carrier in a fixed orientation relative to the first loop. At least one ablating electrode is carried on the second loop for ablating a site of the patient's body where irregular electrical activity occurs.

U.S. Patent Application Publication 2012/0245665, whose disclosure is incorporated herein by reference, describes an electrical lead for a cardiac device including a body having a distal end sized for insertion through a catheter, first and second electrodes extending through the body, with each electrode terminating in a tip having proximal and distal ends and arranged to extend to an area of cardiac tissue. The tips include a fully insulated portion on the proximal and distal ends measuring in a range between 5 percent and 40 percent of the lengths of the tips, and further include an uninsulated intermediate section. The tip of the second electrode includes a helical section surrounding the first electrode and has an insulated portion on an inwardly facing portion surface facing toward the first electrode. The tip of the second electrode also includes a fully insulated portion on the proximal and distal ends measuring in the same or similar percentage range.

A publication entitled "Complete Isolation of Left Atrium Surrounding the Pulmonary Veins: New Insights from the Double-Lasso Technique in Paroxysmal Atrial Fibrillation", Circulation, Vol. 110, No. 15, Oct. 12, 2004, pages 2090-2096, which is incorporated herein by reference, describes a method where Paroxysmal atrial fibrillation (PAF) can be eliminated with continuous circular lesions (CCLs) around the pulmonary veins (PVs).

SUMMARY OF THE INVENTION

An embodiment of the present invention provides a medical probe including a distal end and an elongate body for insertion into an organ of a patient. The distal end is connected to the elongate body and includes multiple arms that, when inserted into the organ, extend to form multiple respective spirals each having electrodes disposed thereon.

In some embodiments, the organ includes a heart, and the electrodes include electrophysiological (EP) mapping electrodes. In other embodiments, each of the multiple arms is configured to conform to a surface of the organ independently of any other of the arms.

In some embodiments, when extended, the spirals are positioned in a plane that is perpendicular to the elongate body. In other embodiments, when extended, the spirals are positioned in a plane that is obliquely oriented relative to the elongate body.

In some embodiments, the multiple arms include four arms that extend at 90-degree orientations relative to one another. In other embodiments, the multiple arms include three arms that extend at 120-degree orientations relative to one another. In yet other embodiments, the multiple arms include two arms that extend at 180-degree orientations relative to one another.

In some embodiments, the electrodes are disposed on the arms with an even pitch. In other embodiments, the electrodes are disposed on the arms with an uneven pitch.

In some embodiments, the electrodes are disposed on a first arm with a first pitch, and on a second arm with a second pitch that is different from the first pitch. In other embodiments, the electrodes include at least one ablation electrode.

In some embodiments, the distal end includes at least one position sensor for measuring a position of the distal end in the organ. In other embodiments, the distal end includes at least one electrical-current electrode for measuring a position of the distal end in the organ.

There is also provided, in accordance with an embodiment of the present invention, a method including inserting a medical probe having an elongate body into an organ of a patient. After insertion into the organ, a distal end of the medical probe is extended to form multiple spiral arms each having electrodes disposed thereon. The spiral arms are placed against a surface of the organ, so as to form contact between the electrodes and the surface. A medical procedure is applied to the surface using the electrodes.

The present invention will be more fully understood from the following detailed description of the embodiments thereof, taken together with the drawings in which:

DETAILED DESCRIPTION OF EMBODIMENTS

Overview

In medical procedures such as cardiac electrophysiological (EP) mapping, one or more electrodes are disposed at the distal end of a medical probe, such as a catheter, and are placed in contact with the surface of a target region in an organ, typically a heart cavity or chamber. Some types of catheters are pre-shaped such that the distal end attains a desired form when entering the heart cavity, such as Lasso-NAV ECO catheters, produced by Biosense Webster Inc. (Diamond Bar, Calif.), whose specification is incorporated herein by reference. The multiple electrodes on the pre-shaped distal end touch multiple respective points on the surface of the organ simultaneously for success in measuring the EP signals during the mapping procedure.

If, however, the area of the lasso spiral is large, the achievable density of the electrodes on the tissue surface is relatively small, thus degrading the electrode coverage. Moreover, when using a single large spiral, the contact quality of the multiple electrodes with the surface may degrade as the lasso spiral cannot conform perfectly to the contour of the surface of the target organ, e.g., due to the stiffness of the catheter spiral over a large area.

Embodiments of the present invention that are described herein provide improved catheter designs, which provide dense coverage of the tissue by the electrodes, as well as high-quality contact with tissue, over a large surface area. In the embodiments described herein, the catheter distal end comprises two or more arms, each having a spiral shape. Each arm comprises one or more EP mapping electrodes that are distributed along the spiral. When the distal end assumes its extended shape, the arms fan-out to cover a large surface area of the tissue.

Each arm, however, is attached separately to the catheter body. Thus, each arm can adapt and flexibly conform separately to the tissue surface. Moreover, the electrode count on the two or more arms is larger than that of a single spiral or lasso covering the same surface area. Thus, when using the disclosed catheter designs, a higher density EP mapping points can be performed simultaneously over a large target region, thus speeding up the overall duration of the therapeutic procedure, without compromising tissue contact quality.

System Description

Figure 1:
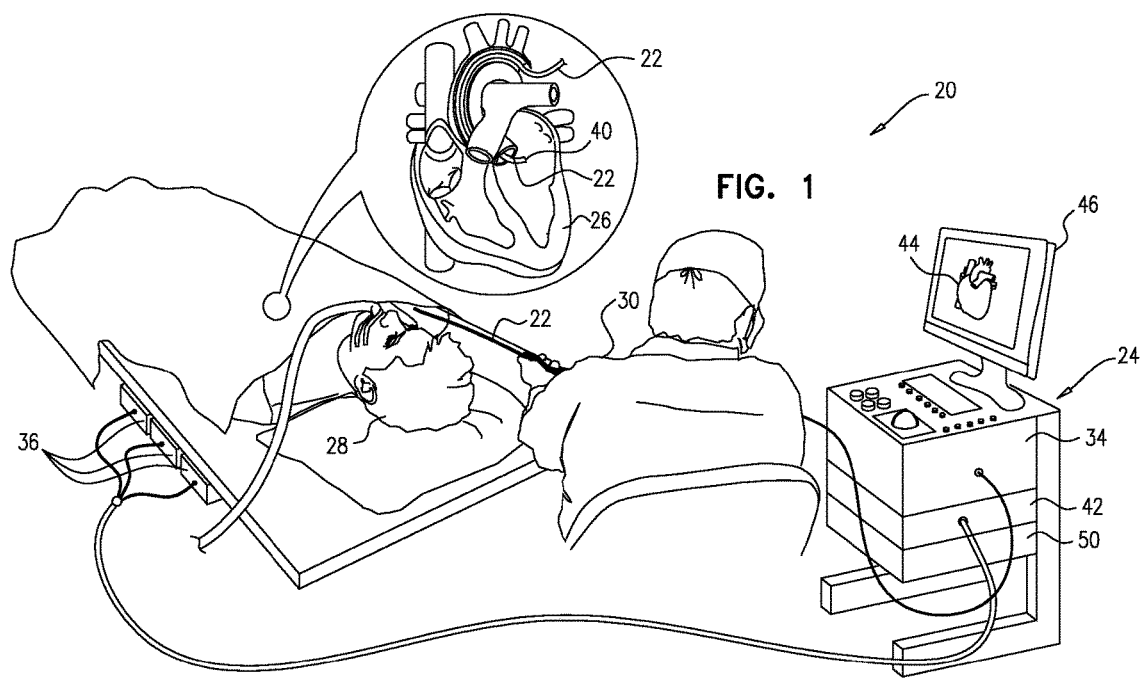
FIG. 1 is a block diagram that schematically illustrates a system for cardiac mapping, in accordance with an embodiment of the present invention.

FIG. 1 is a block diagram that schematically illustrates a system 20 for cardiac mapping, in accordance with an embodiment of the present invention. System 20 comprises a probe 22, in the present example a cardiac catheter, and a control console 24. In the embodiment described herein, it is assumed by way of example that probe 22 may be used for cardiac mapping of a cavity of a heart 26 of a patient 28 for the diagnosis of cardiac dysfunctions, such as cardiac arrhythmias. Alternatively or additionally, probe 22 may be used for other suitable therapeutic and/or diagnostic purposes, such as ablation of tissue in heart 26.

Console 24 comprises a processor 42, typically a general-purpose computer, with suitable front end and interface circuits for receiving signals from probe 22 and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

An operator 30, typically a physician, inserts probe 22 through the vascular system of patient 28. Operator 30 moves a distal end 40 of probe 22 in the vicinity of the target region in heart 26. The probe contacts the surface of the heart cavity with the multiple electrodes at multiple points (map points) in the target region and records the EP signals at the multiple points. In some embodiments, the recorded EP signals at the multiple points are used to build a mapping of the EP signals along the surface of the heart cavity.

The position of the distal end of the probe in the heart cavity is measured typically with a magnetic position sensing system. In this case, console 24 comprises a driver circuit 34, which drives magnetic field generators 36 placed at known positions external to patient 28, e.g., below the patient's torso. A magnetic field sensor, typically a magnetic probe coils (not shown), is attached to probe 22 near distal end 40. The probe sensor generates electrical position signals in response to the magnetic fields from the coils, thereby enabling processor 42 to determine the position, i.e., the location and typically also the orientation, of the distal end 40 within the heart cavity.

In other embodiments, system 20 may use impedance-based position sensing techniques (e.g., advanced catheter location (ACL) technologies) to determine the position of distal end 40 within the heart cavity. System 20 in these embodiments is configured to drive current between at least one current electrode at distal end 40 and a plurality of body surface electrodes on patient 28 (not shown in FIG. 1) typically attached to the patient's chest above the heart. System 20 then determines the position of the distal end based on the measured currents between the plurality of body surface electrodes and the at least one current electrode at distal end 40.

Processor 42 uses the coordinates of the map points to construct a simulated surface of the cardiac cavity, or chamber, in question. Processor 42 then combines the electrical potential measurements of the map points with the simulated surface to produce a map of the potentials overlaid on the simulated surface. Processor 42 displays an image 44 of the map to operator 30 on a display 46, which is used by operator 30 in evaluating local heart dysfunction.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Flexible Multiple-Arm Diagnostic Catheter

Figure 2:
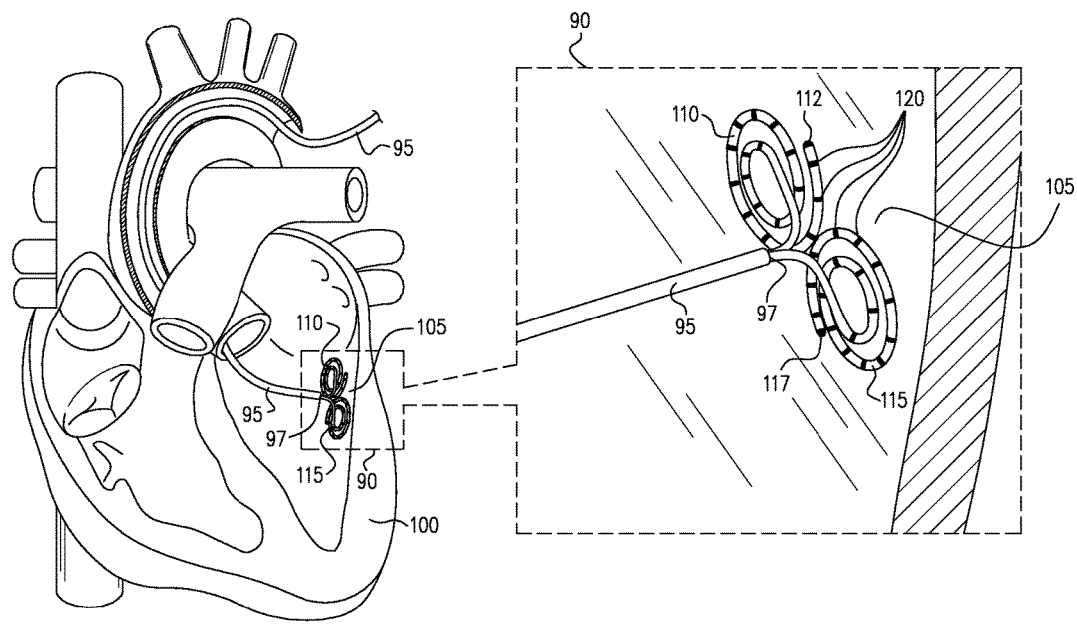
FIG. 2 is a diagram illustrating a multiple-arm catheter for cardiac mapping, in accordance with an embodiment of the present invention.

FIG. 2 is a diagram illustrating a multiple-arm catheter for cardiac mapping, in accordance with an embodiment of the present invention. The multiple-arm catheter, which is shown in the dotted inset 90 in FIG. 2, can be used for implementing catheter 22 of FIG. 1. In the present example, the catheter comprises a sheath 95 with a sheath distal edge 97, which is inserted through the vascular system into a chamber of a heart 100. Sheath distal edge 97 is shown in FIG. 2 positioned close to a surface 105 of heart 100.

The catheter further comprises an elongate catheter body or tube that is inserted through sheath 95. Operator 30 inserts the catheter through the lumen of the sheath. The distal end of the catheter is pre-shaped, such that when the distal end exits sheath distal edge 97, the catheter distal end assumes a predefined shape comprising multiple spiral arms. In their extended positions, the arms are typically oriented in a plane that is perpendicular to the axis of the catheter. However in some embodiments, the arms are positioned in a plane that is obliquely oriented relative to the axis of the catheter (e.g., the elongate body).

The exemplary embodiment shown in FIG. 2 comprises two spiral arms 110 and 115, having distal ends 112 and 117, respectively. In this example the two arms spiral out into 180-degree opposite directions. Multiple electrodes 120 are disposed on arms 110 and 115. In the present example, although not necessarily, the two arms have the same inter-electrode spacing, or pitch (distance between adjacent electrodes).

The two spiral arms are connected to the catheter body (the connection point in the figure is around the point where the catheter exits sheath 95). Each arm is typically flexible at least at this point, and usually elsewhere along the distal end. In particular, the spiral arms are free to conform to surface 105 independently of one another.

As noted above, the use of multiple independently-conforming spiral arms increases the distal end's flexibility, and thus the contact quality of the multiple electrodes with the heart tissue on surface 105. In one catheter placement, a large area of heart tissue can be EP mapped simultaneously. Thus, the disclosed catheter designs shorten the duration of the EP mapping procedure, without degrading contact quality.

In some embodiments, the positions of the multiple electrodes disposed on the spiral arms can be determined by measuring the positions of one or more magnetic position sensors (not shown in the figure) placed in any suitable configuration on or near the arms.

The embodiment shown in FIG. 2 is depicted purely for the sake of conceptual clarity and not by way of limitation of the embodiments of the present invention. In alternative embodiments, the catheter may comprise any suitable number of pre-shaped arms in any suitable predefined orientation. For example, the catheter may comprise four spiral arms that fan out in a predefined orientation of 90 degrees over four respective quadrants to form a flexible "four-leaf clover-like" footprint. As another example, the catheter may comprise three spiral arms that fan out in a predefined orientation of 120 degrees respectively to one another. The arms may have the same size (e.g., covered tissue surface area) or different sizes.

In the present example, the catheter is inserted through sheath 95. In alternative embodiments, the catheter may be inserted using alternative means, for example using a suitable guide-wire.

In some embodiments, electrodes 120 can be arranged in any suitable configuration along the spiral arms, such as electrodes with an evenly-spaced predefined pitch (as in FIG. 2), or electrodes spaced with a variable pitch along the arms. The electrodes can generally be disposed evenly or unevenly.

In other embodiments, electrodes 120 may have a different pitch in different arms, so as to configure the density of the multiple electrode contact points on surface 105. Target regions contacted by more electrodes have a dense EP mapping, whereas contact regions contacted with fewer electrodes have a sparse EP mapping. For example, sparse EP mapping may be used around the ostium of the pulmonary vein into the left atrium, whereas dense EP mapping may be used along the region of the left atrium chamber wall near the ostium.

In yet other embodiments, some of electrodes 120 near distal ends 112 and 117 of arms 110 and 115, respectively, may also comprise any suitable number of ablation electrodes, in addition to the EP mapping electrodes. In this embodiment, a first set of one or more EP mapping electrodes and a second set of one or more ablation electrodes, different from the first set, are disposed on one or more of the catheter arms.

Although the embodiments described herein mainly address flexible multiple-arm catheters for use in cardiac therapies, the methods and systems described herein can also be used in other suitable diagnostic, therapeutic, or imaging applications using medical probes, such as in the kidneys or urinary tract, for example.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A medical probe, comprising:
   an elongate body for insertion into an organ of a patient, the elongate body comprising a distal end; and
   multiple arms that, when arranged to extend from the distal end, are pre-shaped to form multiple spirals that extend away from the distal end and from one another in a common plane, each arm of the multiple arms having electrodes disposed thereon;
   wherein the electrodes are disposed on the arms with an uneven distance between adjacent electrodes.

2. The medical probe according to claim 1, wherein the organ comprises a heart, and wherein the electrodes comprise electrophysiological (EP) mapping electrodes.

3. The medical probe according to claim 1, wherein each of the multiple arms is configured to conform to a surface of the organ independently of any other of the arms.

4. The medical probe according to claim 1, wherein the common plane is perpendicular to the elongate body.

5. The medical probe according to claim 1, wherein the common plane is obliquely oriented relative to the elongate body.

6. The medical probe according to claim 1, wherein the multiple arms comprise four arms that extend at 90-degree orientations relative to one another.

7. The medical probe according to claim 1, wherein the multiple arms comprise three arms that extend at 120-degree orientations relative to one another.

8. The medical probe according to claim 1, wherein the multiple arms comprise two arms that extend at 180-degree orientations relative to one another.

9. The medical probe according to claim 1, wherein the electrodes are disposed on the arms with an even pitch.

10. The medical probe according to claim 1, wherein the electrodes comprise at least one ablation electrode.

11. The medical probe according to claim 1, wherein the distal end comprises at least one position sensor for measuring a position of the distal end in the organ.

12. The medical probe according to claim 1, wherein the distal end comprises at least one electrical-current electrode for measuring a position of the distal end in the organ.

13. A method, comprising:
   inserting a medical probe having an elongate body into an organ of a patient, the elongate body comprising a distal end;
   after insertion into the organ, extending multiple spiral arms away from the distal end relative to one another in a common plane each arm having electrodes disposed thereon;
   placing the spiral arms against a surface of the organ, so as to form contact between the electrodes and the surface; and
   applying a medical procedure to the surface using the electrodes.

14. The method according to claim 13, wherein the organ comprises a heart, wherein the electrodes comprise electrophysiological (EP) mapping electrodes, and wherein applying the medical procedure comprises measuring EP potential using the EP mapping electrodes.

15. The method according to claim 13, wherein placing the spiral arms comprises causing each of the arms to conform to a surface of the organ independently of any other of the arms.

16. The method according to claim 13, wherein the common plane is perpendicular to the elongate body.

17. The method according to claim 13, wherein the common plane is obliquely oriented relatively to the elongate body.

18. The method according to claim 13, wherein the spiral arms comprise one of:
   four arms that extend at 90-degree orientations relative to one another;
   three arms that extend at 120-degree orientations relative to one another; and
   two arms that extend at 180-degree orientations relative to one another.

19. The method according to claim 13, wherein the electrodes are disposed on the arms with an even pitch.

20. The method according to claim 13, wherein the electrodes are disposed on the arms with an uneven pitch.

21. The method according to claim 13, wherein the electrodes are disposed on a first arm with a first pitch, and on a second arm with a second pitch that is different from the first pitch.

22. The method according to claim 13, wherein the electrodes comprise at least one ablation electrode, and wherein applying the medical procedure comprises ablating the surface using the at least one ablation electrode.

23. The method according to claim 13, wherein the distal end comprises at least one position sensor, and comprising measuring a position of the distal end in the organ using the position sensor.

24. The method according to claim 13, wherein the distal end comprises at least one electrical-current electrode, and comprising measuring a position of the distal end in the organ using the current electrode.

25. A medical probe, comprising:
   an elongate body for insertion into an organ of a patient, the elongate body comprising a distal end; and
   multiple arms that, arranged to extend from the distal end, are pre-shaped to form multiple spirals that extend away from the distal end and from one another in a common plane, each arm of the multiple arms having electrodes disposed thereon;
   wherein the electrodes are disposed on a first arm with a first distance between adjacent electrodes, and on a second arm with a second distance between adjacent electrodes that is different from the first distance.

26. A medical probe, comprising:
   an elongate body for insertion into an organ of a patient, the elongate body comprising a distal end; and
   multiple arms that, when arranged to extend from the distal end, are pre-shaped to form multiple spirals that extend away from the distal end and from one another in a common plane, each arm of the multiple arms having electrodes disposed thereon.

* * * * *